United States Patent [19]
Khan

[11] 3,951,953
[45] Apr. 20, 1976

[54] PHARMACEUTICAL COMPOSITIONS
[75] Inventor: Mohammad Zafar Khan, Worthing, England
[73] Assignee: Beecham Group Limited, Great Britain
[22] Filed: July 8, 1974
[21] Appl. No.: 486,713

[30] Foreign Application Priority Data
July 10, 1973 United Kingdom............... 32769/73

[52] U.S. Cl............................. 260/239.1; 424/271
[51] Int. Cl.$^2$............... C07D 499/68; C07D 499/70
[58] Field of Search ...................... 260/239.1, 2.1 E

[56] References Cited
FOREIGN PATENTS OR APPLICATIONS
856,501  12/1960  United Kingdom.............. 260/239.1

Primary Examiner—Gerald A. Schwartz

[57] ABSTRACT

Complexes of a semi-synthetic penicillin and an anion exchange resin cross-linked less than 4% and wherein the penicillin, with or without a non-complexed additional penicillin, is absorbed onto and in the ducts or channels in the resin particles substantially all of which have diameters between 20 $\mu$ and 250 $\mu$. The semi-synthetic penicillin constitutes 35–65% of the complex. The complexes are formulated as pharmaceutical compositions which can be in tablet or syrup form. The penicillin is released rapidly and completely and is free of unpleasant taste.

5 Claims, No Drawings

PHARMACEUTICAL COMPOSITIONS

The present invention relates to pharmaceutical preparations. More specifically, this invention relates to compositions comprising complexes of semi-synthetic penicillins and resins and to the novel complexes themselves.

British Pat. No. 856,501 disclosed pharmaceutical preparations of the natural penicillins benzylpenicillin (Penicillin G) or phenoxymethylpenicillin (Penicillin V) which preparations had unobjectionable taste. The preparations comprised a complex of non-toxic anion exchange resin onto which the penicillin was absorbed. It was demonstrated that the objectionable taste of the penicillin had been reduced or eliminated because the resin only released the absorbed penicillin very slowly thereby preventing a sufficient build-up of the penicillin in the mouth to cause an unpleasant taste. In fact, it was suggested that the release rate of the penicillins from the complexes was sufficiently slow for compositions containing them to be suitable for use as sustained release preparations. It has since been shown that slow release of penicillins from formulations which are administered orally, usually results in a significant reduction in the amount of penicillin which is absorbed into the bloodstream so that the compositions of British Pat. No. 856,501 suffer from a serious disadvantage.

There have now been discovered complexes which may be used in the preparation of formulations of synthetic penicillins which have a considerably less objectionable taste than the formulations containing the semi-synthetic penicillins themselves and which give a rapid and essentially complete release of the semi-synthetic penicillin into the gastro-intestinal tract. Rapid release of the semi-synthetic penicillin from such complexes into the gastro-intestinal tract has not previously been described. It was thought surprising that these new complexes should have such different properties from the prior art complexes of British Pat. No. 856,501 but repeated tests have confirmed these unexpected results.

Accordingly, the present invention provides a complex in the form of finely divided particles which particles comprise 20–70% of a semi-synthetic penicillin as hereinafter defined and 30–80% of an anion-exchange resin as hereinafter defined in which complex the penicillin is absorbed onto the surface of, and in the ducts or channels in, the resin particles and substantially all of said particles have diameters between $20\mu$ and $250\mu$.

When used herein, "substantially all" means at least 90%, most suitably, 95% and preferably 99%.

Suitably, the particles have diameters between $40\mu$ and $250\mu$, more suitably, between $40\mu$ and $150\mu$ and preferably, between $40\mu$ and $100\mu$.

Resins suitable for use in this invention are water-insoluble benzene-insoluble, pharmaceutically acceptable, strongly basic, highly-porous anion-exchange resins containing less than 4% of cross-linking.

Suitable resins may be prepared by inter alia, the method of U.S. Pat. No. 3,006,866. One particularly suitable resin is Dowex 1 - X2 (manufactured by Dow Chemical Co.) which is a polymer of styrene cross linked at a level of 2% with divinylbenzene and $-N(CH_3)_3+$ quaternary ammonium groups. Other similar resins currently available which are suitable include Serolit FF-IP-SRA 64 (manufactured by Rohm and Ha as Limited) and Lewatit OC 1008 (manufactured by Bayer Chemicals.).

Suitable semi-synthetic penicillins for inclusion in the complex of this invention are those containing a free carboxylic group. Such penicillins will be in the form of their anions when present in the complex. Examples of suitable penicillins include cloxacillin, dicloxacillin, flucloxacillin and the phenyl and 5-indanyl esters of carbenicillin and ticarcillin.

In general, as it is preferable to keep formulation aids as low as possible, the quantity of semi-synthetic penicillin present in the the complex is kept as high as is readily obtainable. However, as standardization is not always absolutely certain at high proportions of penicillin, it has been found that preferred complexes of the invention comprise 35% to 65% of semi-synthetic penicillin and 35% to 65% of resin.

The capacity and rates of release and uptake of the semi-synthetic penicillin are dependent on inter alia, the cross-linking in the resin. To achieve high capacities and rapid exchange, the cross-linking should be below 3%. However, since resins with very small amounts of cross-linking tend to absorb and retain water to an unacceptable extent, resins containing above 1% cross-linking are generally used.

Thus, preferred resins for use in this invention will contain from 1% to 3% of cross-linking, for example, about 2% cross-linking.

Particularly acceptable release rates 'in vitro' and penicillin serum concentrations 'in vivo' are generally obtained from particles substantially all of which have a diameter between $40\mu$ and $100\mu$ (minus 150, plus 400 mesh): this may be seen from Tables 1 and 2 which respectively illustrate the effect of particle size on the release rate of flucloxacillin 'in vitro' and the blood levels achievable 'in vivo'.

TABLE 1

The effect of particle size of flucloxacillin resin complex on the release rate of flucloxacillin in 0.05M Sodium Acetate solution at 37°C.

| MESH SIZE* | | | | | |
|---|---|---|---|---|---|
| −30 +36 | | −36 +44 | −44 +60 | −240 +425 | |
| Time (min) | % release | % release | % release | Time (min) | % release |
| 20 | 27.6 | 34.2 | 35.1 | 5 | 20.6 |
| 40 | 44.1 | 49.6 | 54.6 | 10 | 43.3 |
| 60 | 55.2 | 61.3 | 67.1 | 20 | 55.1 |
| 80 | 64.8 | 70.0 | 76.3 | 30 | 68.0 |
| 100 | 71.5 | 76.4 | 82.5 | 45 | 80.2 |
| 120 | 77.6 | 82.1 | 87.4 | 60 | 88.7 |
| 140 | 83.0 | 86.0 | 90.5 | 75 | 94.9 |
| 160 | 85.3 | 88.9 | 93.9 | 90 | 97.3 |
| 180 | 88.1 | 91.9 | 96.1 | 105 | 98.1 |
| 200 | 89.1 | 93.3 | 97.8 | 120 | 100.0 |

*The various particle size fractions were obtained by passing the complex (as beads) through the given British standard mesh sieve except the minus 240 mesh sample which was ground before sieving.

TABLE 2

Bioavailability after 10 ml. of syrup containing 125 mg. of flucloxacillin as resin complex (size range $60\mu$ to $100\mu$) was administered to volunteers.

| Time After Dosing (min.) | 20 | 40 | 60 | 90 | 120 | 240 |
|---|---|---|---|---|---|---|
| Fluclox.Serum Conc. ($\mu$g/ml) | | 4.0 | 6.5 | 5.4 | 3.7 | 1.6 | <1.6 |

The mean percentage of dose recovered from the urine as flucloxacillin in the period up to 6 hours after dosing was 51%.

These results indicate that a substantial proportion of the administered dose was rapidly released from the syrup and absorbed, and there was no evidence of prolonged release. Thus, the complexes of this invention differ surprisingly and substantially from previously known complexes.

In a preferred aspect, the present invention comprises a complex in the form of finely divided particles substantially all of which have diameters in the range $40\mu$ to $100\mu$ which complex consists of 35%–65% of cloxacillin, dicloxacillin, flucloxacillin or the phenyl or 5-indenyl $\alpha$-ester of carbenicillin and 35%–65% of an anion-exchange resin as hereinbefore described which has from 1% to 3% cross-linking. More preferably, the complex consists essentially of 45%–55% penicillin and 45%–55% resin.

Complexes comprising about 50% semi-synthetic penicillin and about 50% resin are particularly suitable.

The complexes of the invention may be prepared by contacting a solution of the semi-synthetic penicillin as a water soluble salt with the resin and thereafter separating the complex. The desired particle size may be achieved in one of three ways. In the first of these, the resin in the form of beads in the size range 0.1 to 12 mm (−14 to +150 mesh) is treated with a solution of the salt of the penicillin and the resulting complex milled to the required particle size. In the second, resin previously milled to the desired size is treated with the solution of the salt of the penicillin. In the third and preferred method, beadlets of the resin of the desired particle size are treated with the penicillin solution.

One suitable method of contacting the resin and penicillin solution comprises passing a 0.5%–15% solution of a water-soluble salt of the penicillin through a column containing the resin until the resin has absorbed the desired amount of penicillin. (This may be determined by monitoring the effluent).

A further invitable method of contacting the resin and penicillin solution comprises slurrying the resin with the 0.5%–15% solution of the water-soluble salt of the penicillin.

The step of washing the surface of the complex with a solution of an electrolyte as described in British Pat. No. 856,501, has not been found to be always advantageous. However, washing with electrolyte free water frequently leads to a product of reduced taste.

One use for the complexes of this invention is in powders or granules for later reconstitution into syrups. The granules may also be consumed in the dry state. When used in such powders or granules, the complexes have the property of not releasing the absorbed semi-synthetic penicillin in the aqueous medium used to make up the syrup but of providing ready release of the semi-synthetic penicillin in the gastro-intestinal tract. Further uses for the complexes of the invention are in tablet formulations intended to be chewed or dispersed in water and the resulting suspensions swallowed.

Such reconstitutable powders and granules are included within the scope of this invention.

Accordingly, in one aspect, the present invention provides powder or granules suitable for reconstitution to pharmaceutical syrups which powder or granules comprise 2.5%–50% of a complex of the invention 0–5% of ionic conventional excipients, 0–25% of a further penicillin and 40%–97.5% of non-ionic conventional excipients.

Suitable conventional excipients include flavouring agents, colouring agents, preserving agents, buffering agents, suspending agents, stabilising agents or other excipients commonly used in the preparation of reconstitutable powders or granules.

In a further aspect, the invention provides tablets which may be chewed or dispersed in water and the resulting suspension swallowed. Such a tablet comprises 5%–40% of a complex of the invention and 60%–95% of non-ionic conventional excipients. Suitable conventional excipients include lubricants, disintegrants, binders, flavouring, sweetening and colouring agents, or other excipients commonly used in the preparation of chewable and dispersable tablets.

Flavouring agents may be natural or synthetic and also include sweetening agents such as sodium saccharin neohesperidin dihyavochalcone or the like.

In reconstitutable powders or granules designed for dose volumes of 5–10 ml., the complex of the invention is generally present by from 5%–25%; in reconstitutable powders or granules designed for dose volumes of 2 ml. or less, for example, in paediatric suspensions, the complex of the invention is generally present by from 15%–50%.

Suitable further penicillins for inclusion within the reconstitutable powders and granules include ampicillin and amoxycillin and their phthalidyl or pivaloyloxymethyl esters.

The complex used in reconstitutable powders and granules should not contain significant numbers of particles of diameters greater than $75\mu m$ in order to avoid an unpalatable feeling of grittiness in the mouth.

Preferably, if a further penicillin (i.e. a non-complexed penicillin) is present, it is amoxicillin or ampicillin. Mixtures of cloxacillin or flucloxacillin (as the complexed penicillin) with ampicillin or amoxicillin (as the non-complexed penicillin) are particularly suitable. Thus, certain preferred reconstitutable powders or granules designed for dose volumes of 5–10 ml., or more comprise 5–25% of a complex in the form of discrete particles substantially all of which have diameters of $40\mu m$ to $75\mu m$ and which consist of 35–65% of cloxacillin or flucloxacillin and 35–65% of an anion exchange resin as hereinbefore defined which has 1–3% of cross-linking, 60–95% sucrose; 0–7.5% of other conventional excipients and 0–10% of ampicillin, amoxycillin, or esters of ampicillin or amoxycillin, for example the phthalidyl or pivaloyloxymethyl esters.

Further, certain preferred reconstitutable powders or granules more suitable for dose volumes of 2ml. or less comprise 15–50% of a complex in the form of discrete particles substantially all of which have diameters of 40 $\mu m$ to 75 $\mu m$ and which consist of 35–65% of cloxacillin or flucloxacillin and 35–65% of an anion exchange resin as hereinbefore defined which has 1–3% of cross-linking, 20–75% of sucrose, 0–75% of other conventional excipients and 0–20% of ampicillin, amoxycillin, or esters of ampicillin or amoxycillin for example, the phthalidyl esters.

Preferred formulations of chewable or dispersible tablets comprise 15 to 25% of a complex in the form of discrete particles substantially all which have diameters of $40\mu$ to $75\mu$, and which consist at 35–65% of cloxacillin or flucloxacillin and 35–65% of an anion exchange resin as hereinbefore defined which 1–3% of cross-linking, and 75 to 85% of conventional excipients.

Preferably, all such compositions contain less than 2% of ionic excipient

The following Examples illustrate the invention:

EXAMPLE 1

An amount equivalent to a 50g. dry weight of the resin of Example 1 of U.S. Pat. No. 3,006,866 currently available as 'Lewatit OC 1008' from Bayer Chemicals Limited, in the chloride form and in the −14+50 mesh range were suspended in 100 mls. of distilled water and put into a column 2 cm. wide, and 30 cm. long. Deionised water (200 mls.) was passed through the column followed by 8 l. of a 1% solution of sodium flucloxicillin which was passed through the column at a rate not exceeding 25 mls. per minute followed by 1 l. of deionised water. The effluent solution was collected and the quantity of absorbed penicillin determined. This indicated that the resin had absorbed approximately its own weight of the flucloxacillion anion. The residual flucloxacillin in the effluent can be recovered for further use.

The damp complex was milled to a powder 90% of the particles of which had diameters of from 75 $\mu$ to 150 $\mu$ and subsequently dried.

EXAMPLE 2

Lewatit OC 1008 (50g dry weight) in the chloride form and in the −14 +50 mesh range was suspended in deionised water (300 mls.) and washed thoroughly by agitation. The water was drained off and a solution of sodium cloxacillin (5 l. 1% w/v cloxacillin ion) was added and the suspension stirred for 2½ hours. The solution was drained off and replaced with fresh solution (3 l.). This suspension was stirred for a further 2½ hours and the solution drained off. The resulting complex was washed with water (two portions of 500 ml.) to remove any unabsorbed penicillin and milled and dried as described in Example 1.

(Determination of the unabsorbed cloxacillin from discarded solutions and washings indicated that the final complex contained approximately 50% resin and 50% penicillin).

EXAMPLE 3

The procedure of Example 2 was repeated replacing the sodium cloxacillin with sodium flucloxacillin. The resulting complex contained 48 ± 3% flucloxacillin anion.

EXAMPLE 4

Dowex 1 - X2 (100 g dry weight) currently available from the Dow Chemical Co in the chloride form and as beads of - 230 mesh particle size is also stirred with a solution of sodium flucloxacillin (12, 10% w/v flucloxacillin ion) in deionised water for 30 minutes. The suspension was filtered and the beads were restirred with deionised water (12), for 15 minutes. The suspension was filtered and the complex was washed thoroughly with deionised water (2 ml.) and dried. The resulting complex contained 47 ± 3% of flucloxacillin anion.

EXAMPLE 5

The procedure of Example 3 was repeated on a one tenth scale, replacing sodium flucloxacillin with sodium cloxacillin. The resulting complex contained 45 ± 3% of cloxacillin anion.

EXAMPLE 6

The procedure of Example 4 was repeated, replacing sodium flucloxacillin with sodium α phenoxycarbonize benzylpenicillin. The resulting complex contained 44 ± 3% of the penicillin anion.

EXAMPLE 7

The following powder was prepared —

| | |
|---|---|
| A complex of Examples 1, 3 or 4 equivalent to active penicillin | 1.60 g |
| Preservatives | 0.10 g |
| Stabilisers | 0.04 g |
| Buffering Agents | 0.20 g |
| Suspending Agents | 0.10 g |
| Flavours, sweeteners, colours | 0.60 g |
| Amoxycillin Trihydrate equivalent to Amoxycillin | 1.60 g |
| Caster Sugar | to 40 g |

This powder may be reconstituted with water to produce 60 ml. of syrup.

EXAMPLE 8

The following powder suitable for reconstitution into a penicillin syrup was prepared —

| | |
|---|---|
| A complex of Examples 1, 2, 3, 4 or 5 equivalent to active penicillin | 1.60 g. |
| Preservatives | 0.10 g. |
| Stabilisers | 0.04 g. |
| Buffering Agents | 0.24 g. |
| Flavours, sweeteners and colours | 0.80 g. |
| Suspending Agents | 0.10 g. |
| Caster Sugar | to 45 g. |

This powder may be reconstituted with water to provide 60 mls. of syrup.

EXAMPLE 9

Powder from Example 8 was converted into granules by blending with a solution (14.5 ml.) of hydro propyl cellulose (50 mg) in isopropyl alcohol (15.0 ml.). The granules were partially dried, passed through a 22 mesh sieve and further dried.

The granules may be reconstituted with water to produce 60 ml. of syrup.

EXAMPLE 10

| | |
|---|---|
| A complex of Example 4 equivalent to active penicillin | 1.05 g. |
| Preservatives | 0.02 g. |
| Stabilisers | 0.03 g. |
| Flavours, sweeteners and colours | 0.03 g. |
| Suspending Agents | 0.02 g. |
| Buffering Agents | 0.03 g. |
| Caster Sugar to | 6.00 g. |

This powder may be reconstituted with water to produce 10 ml. syrup.

EXAMPLE 11

A CHEWABLE OR DISPERSABLE TABLET

| | |
|---|---|
| A complex of Example 4 equivalent to active penicillin | 125 mg. |
| Lubricant | 10 mg. |
| Disintegrant | 100 mg. |
| Binder | 4 mg. |
| Flavours and Sweeteners | 52 mg. |
| Colour | 8 mg. |

| | |
|---|---|
| -continued | |
| Buffering Agent | 500 mg. |

What we claim is:

1. A complex in the form of finely divided particles which particles comprise 20%–70% of cloxacillin, dicloxacillin, flucloxacillin or the phenyl or 5-indanyl α-esters of carbenicillin or ticarcillin and 30%–80% of a water-insoluble, benzene-insoluble, pharmaceutically acceptable, strongly basic, highly porous anion exchange resin having less than 4% of cross-linking in which complex the penicillin is absorbed onto the surface of an in the ducts or channels in the resin particles and substantially all of said particles have diameters between $20\mu$ and $250\mu$.

2. A complex as in claim 1 wherein substantially all of the complex particles have diameters between $40\mu$ and $100\mu$.

3. A complex as in claim 2 which comprises 35%–65% of cloxacillin, dicloxacillin, flucloxacillin or the phenyl or 5-indanyl α-esters of carbenicillin or ticarcillin and 35%–65% of the anion exchange resin.

4. A complex as in claim 3 wherein the resin has from 1%–3% cross-linking.

5. A complex as in claim 4 which comprises 50% of cloxacillin, dicloxacillin, flucloxacillin or the phenyl or 5-indanyl α-esters of carbenicillin or ticarcillin and 50% of the anion exchange resin.

* * * * *